(12) United States Patent
Lee et al.

(10) Patent No.: US 8,614,362 B2
(45) Date of Patent: *Dec. 24, 2013

(54) PROCESS FOR PREPARING IODINATED AROMATIC COMPOUNDS

(75) Inventors: Joong-ki Lee, Seoul (KR); Han-Seok Kim, Gyeonggi-do (KR); Jae-Bong Lim, Gyeonggi-do (KR); Il-Hoon Cha, Gyeonggi-do (KR)

(73) Assignee: SK Chemicals Co., Ltd. (KR)

( * ) Notice: Subject to any disclaimer, the term of this patent is extended or adjusted under 35 U.S.C. 154(b) by 266 days.

This patent is subject to a terminal disclaimer.

(21) Appl. No.: 13/133,904

(22) PCT Filed: Dec. 10, 2009

(86) PCT No.: PCT/KR2009/007401
§ 371 (c)(1),
(2), (4) Date: Jun. 9, 2011

(87) PCT Pub. No.: WO2010/068051
PCT Pub. Date: Jun. 17, 2010

(65) Prior Publication Data
US 2011/0245550 A1 Oct. 6, 2011

(30) Foreign Application Priority Data
Dec. 11, 2008 (KR) .................. 10-2008-0126117

(51) Int. Cl.
*C07C 17/00* (2006.01)
(52) U.S. Cl.
USPC .......................................... 570/206; 570/203
(58) Field of Classification Search
None
See application file for complete search history.

(56) References Cited

U.S. PATENT DOCUMENTS

| 4,746,758 | A | | 5/1988 | Rule et al. | |
| 4,778,938 | A | | 10/1988 | Rule et al. | |
| 4,786,713 | A | | 11/1988 | Rule | |
| 4,792,641 | A | * | 12/1988 | Rule et al. | 570/202 |
| 4,810,826 | A | * | 3/1989 | Cook et al. | 570/203 |
| 8,309,775 | B2 | * | 11/2012 | Kim et al. | 570/206 |

FOREIGN PATENT DOCUMENTS

| CN | 87106739 A | 4/1988 |
| CN | 1036197 A | 10/1989 |
| KR | 10-2008-0018356 | 2/2008 |
| WO | WO-88/07509 A1 | 10/1988 |

OTHER PUBLICATIONS

"International Application Serial No. PCT/KR2009/007401, International Search Report mailed Aug. 2, 2010", (w/ English Translation), 4 pgs.
"Chinese Application Serial No. 200980156382.4, Office Action mailed Apr. 2, 2013", 7 pgs.

* cited by examiner

*Primary Examiner* — Sudhakar Katakam
(74) *Attorney, Agent, or Firm* — Schwegman, Lundberg & Woessner, P.A.

(57) ABSTRACT

The present invention relates to a process for preparing iodinated aromatic compounds. Particularly, the present invention comprises the step of performing the iodination of a non-halogenated aromatic compound, a monoiodo aromatic compound, a diiodo aromatic compound, and iodine in the presence of a zeolite catalyst under oxygen atmosphere.

In the process for preparing iodinated aromatic compounds according to the present invention, an iodination and an iodine conversion simultaneously occur, and then prevent side-reactions. Also, the lifetime of an iodination catalyst used therein can be extended by controlling the reaction temperature stably. Therefore, the process can be used for mass production of diiodo compound.

16 Claims, 4 Drawing Sheets

PROCESS FOR PREPARING IODINATED AROMATIC COMPOUNDS

CROSS REFERENCE TO RELATED APPLICATION

This application is a nationalization under 35 U.S.C. 371 of PCT/KR2009/007401, filed Dec. 10, 2009 and published as WO 2010/068051 A2 on Jun. 17, 2010, which application claims priority to and the benefit of Korean Patent Application No. 10-2008-0126117, filed Dec. 11, 2008, which applications and publication are incorporated herein by reference in their entirety.

FIELD OF THE INVENTION

The present invention relates to a process for preparing iodinated aromatic compounds, in which iodination and iodine conversion simultaneously occur to prevent side-reactions. Further, through the process according to the present invention, lifetime of the iodination catalyst is extended by enabling to control the reaction temperature stably during the process, leading to the controlled formation of impurities.

DESCRIPTION OF THE RELATED ART

In various commercial fields, much focus has been placed on the technology of preparing halogenated aromatic compounds by reacting aromatic compounds such as benzene or naphthalene with halogen such as bromine, chlorine, iodine, etc.

Typically, p-dichloro benzene, which is prepared through the reaction of benzene with chlorine, is used as a raw material for the preparation of engineering plastic, polyphenylene sulfide (PPS). Technology of preparing PPS by polymerization of p-dichloro benzene with sodium sulfide in an N-methyl pyrrolidone solvent is known as the Macallum process, and most commercial PPS is currently produced through this Macallum process. However, since it is difficult to obtain a high-molecular-weight polymer only through the Macallum process, a curing process as a post-process is carried out to obtain the high-molecular-weight polymer, and PPS obtained through the curing process is disadvantageous in that it becomes brittle due to a crosslinking reaction or the like. Metal salts such as sodium chloride (NaCl) are also necessarily produced as reaction byproducts in the polymerization process, and cause serious problems in terms of the economic efficiency of commercial processes and the physical properties of the polymer.

As methods which can fundamentally eliminate the production of metal salts and enable linear polymers to be obtained, U.S. Pat. Nos. 4,746,758 and 4,786,713 and related patents suggest methods of directly melt-polymerizing p-diiodobenzene (p-DIB) with sulfur.

As shown in FIG. 1, U.S. Pat. Nos. 4,778,938 and 4,746,758 also disclose methods of preparing p-DIB by reacting benzene with iodine in the presence of oxygen over a zeolite catalyst. These methods are advantageous in high conversion rate, high selectivity to the commercially useful p-diiodo compound, and minimal oxidation of the raw material, benzene or naphthalene.

However, such iodination methods are problematic in controlling the reaction temperature, which is related to a locally occurring massive exothermic reaction. That is, oxidation of hydroiodic acid (HI) is necessarily accompanied with iodination of aromatic compounds in the presence of a zeolite catalyst under oxygen atmosphere. This oxidation of HI is a massive exothermic reaction, which elevates the reaction temperature of the center of a reactor. Under this elevated temperature condition, the oxidation of HI is more accelerated, and thus combustion reaction of reactants also becomes vigorous, bringing about a massive runaway reaction. Furthermore, upon scale-up of the plant to a commercial scale for high productivity, control of reactor temperature becomes a critical issue and is preferentially considered, because the diameter of the reactor should be designed to be sufficiently large.

In addition, under this elevated temperature condition, combustion reaction of the reactants, in accordance with formation of impurities such as carbon deposits, make the catalyst inactive and thus shorten the replacement period of the catalyst. Further, due to the difficulty in the control of the reaction temperature, the feeding flux of the reactants cannot be increased, leading to a drop in productivity of the desired product, diiodo compound.

Therefore, the present inventors have studied on a process for preparing iodinated aromatic compounds, which effectively prevents side-reactions and extends lifetime of the iodination catalyst by enabling stable reaction temperature control during the process, leading to an increase in the production of diiodo compound, thereby completing the present invention.

SUMMARY OF THE INVENTION

It is an object of the present invention to provide a process for preparing aromatic compounds, which prevents side-reactions to control impurity formation, thereby increasing productivity of the desired diiodo compound.

It is another object of the present invention to provide a process for preparing iodinated aromatic compounds, which extends catalyst lifetime by enabling stable reaction temperature control during the process.

Figure 1:
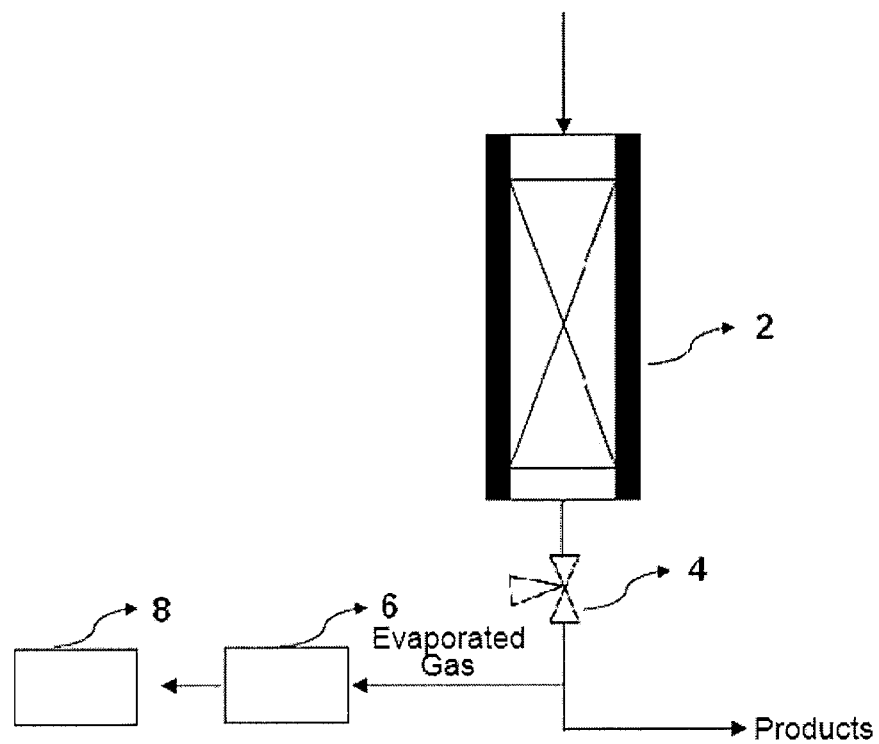
FIG. 1 is a schematic diagram showing the preparation process of iodinated aromatic compounds according to the Comparative Example 1.

2: Iodination reactor
4: Back pressure regulator
6: Sample handling system
8: Gas analyzer
10: Distillation column 1
12: Distillation column 2
14: Distillation column 3
16: Crystallization and solid/liquid separator

DETAILED DESCRIPTION OF THE EMBODIMENTS

The present invention provides a process for preparing iodinated aromatic compounds, comprising the step of performing an iodination of a non-halogenated aromatic compound, a monoiodo aromatic compound, a diiodo aromatic compound, and iodine in the presence of a zeolite catalyst under oxygen atmosphere.

Hereinafter, the process for preparing iodinated aromatic compounds according to the specific embodiment of the present invention will be described in detail.

According to one embodiment of the present invention, a process for preparing iodinated aromatic compounds comprises the step of performing an iodination of a non-halogenated aromatic compound, a monoiodo aromatic compound, a diiodo aromatic compound, and iodine in the presence of a zeolite catalyst under oxygen atmosphere.

The term 'iodination', as used herein, is defined as a reaction of a non-halogenated aromatic compound such as benzene, naphthalene, and biphenyl, a monoiodo compound thereof, and a diiodo compound thereof with iodine molecules, leading to substitution of hydrogen atom of the aromatic compound by iodine atom. Further, the term 'iodine conversion', as used herein, is defined as a reaction of multi-iodo substituted compound (di-, tri-iodo substituted compound) with non-halogenated aromatic compounds, leading to substitution of iodine atom of the multi-iodo substituted compound (di-, tri-iodo substituted compound) by hydrogen atom.

In addition, the term 'non-halogenated aromatic compound', as used herein, is defined as one in which no hydrogen atom of the aromatic compound such as benzene, naphthalene, and biphenyl is substituted with halogen. The term 'monoiodo aromatic compound' or 'monoiodo compound' is defined as one in which any one hydrogen atom of the non-halogenated aromatic compound is substituted by iodine atom, and exemplified by 'monoiodo benzene' or the like. The term 'diiodo aromatic compound' or 'diiodo compound' is defined as one in which any two hydrogen atoms of the non-halogenated aromatic compound are substituted by iodine atoms, and exemplified by 'diiodo benzene' or the like. There are three isomers of the diiodo compound, designated para (p-), ortho (o-), and meta (m-). In addition, the term 'iodinated aromatic compound', which is to be prepared in the present invention, is defined as one resulting from iodination of one or more hydrogen atoms in the non-halogenated aromatic compound, and encompasses monoiodo compound, diiodo compound, and triiodo compound.

In accordance with the process for preparing iodinated aromatic compounds according to the above embodiment, a diiodo aromatic compound is added to a reactant, and thus iodination and iodine conversion simultaneously occur, thereby suppressing side-reactions. Further, the addition of diiodo compound enables stable reaction temperature control during the process, and thus extends catalyst lifetime and suppresses side-reactions, thereby increasing productivity of the diiodo compound.

That is, in accordance with the process of the above embodiment of the present invention, iodination of non-halogenated aromatic compound and iodine conversion simultaneously occur in the presence of a zeolite catalyst under oxygen atmosphere. The reactants are adsorbed on the catalyst, and then produced in the form of iodinated compound after iodination. Simultaneously, as the concentration of diiodo compound introduced to a reactor is increased, iodine conversion of diiodo compound and triiodo compound into monoiodo compound occurs. When the concentration of diiodo compound reaches above a certain level, by-products resulting from side-reactions are found to maintain at a constant level, indicating that iodination and iodine conversion occur at the same time in the presence of a zeolite catalyst.

Meanwhile, the presence of oxygen is essential during the reaction. Hydrogen iodide produced during the iodination should be oxidized to iodine ($I_2$) to participate in the iodination again. Therefore, in the absence of oxygen, or when only a minor amount of oxygen is present in comparison with that of hydrogen iodide, the hydrogen iodide form an azeotrope with water that is produced from the oxidation reaction, which has a harmful effect on the refining process and also causes severe corrosion of the equipment by its strong oxidation reaction. Accordingly, oxygen is required in an amount equal to or greater than the number of moles of iodine used in the reaction.

Figure 2:
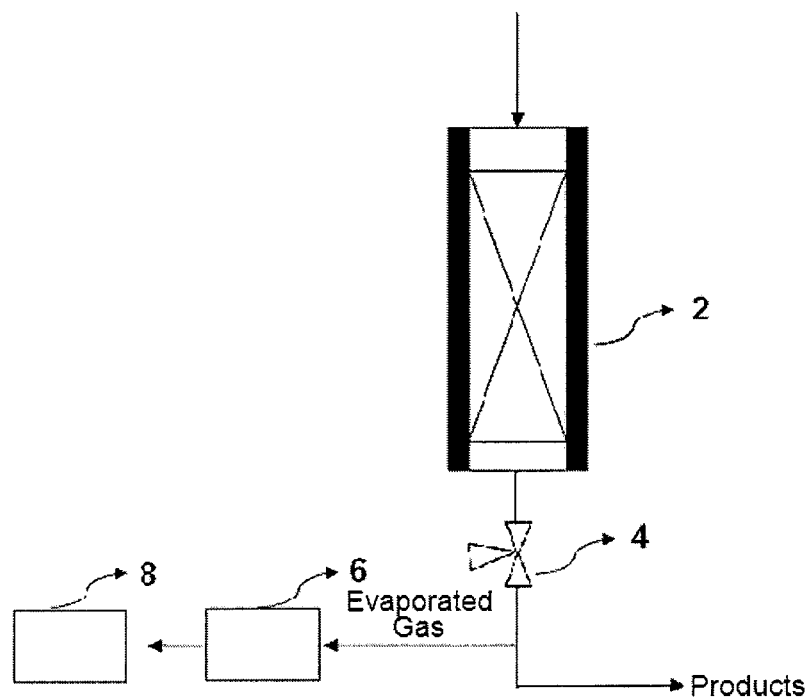
FIG. 2 is a schematic diagram showing the preparation process of iodinated aromatic compounds according to Examples 1 to 3 of the present invention.

The process for preparing iodinated aromatic compounds according to one specific embodiment is briefly illustrated in FIG. 2. In FIG. 2, a back pressure regulator 4 controls the reaction pressure of iodination and makes the pressurization reaction possible, a sample handling system 6 removes vapor included in gas to protect a gas analyzer in a post-process, and a gas analyzer 8 functions to analyze the content of carbon dioxide in gas. In this regard, an iodination reactor 2 may be preferably designed to be surrounded by an oil jacket. In order to maintain the reaction temperature within a predetermined range, the oil jacket is filled with oil, and it absorbs elevated heat due to the iodination and recycles it to the upper part of the oil jacket where it is recovered. Through this process, the reaction temperature of the iodination reactor 2 can be controlled.

The diiodo compound may be prepared or purchased to be used as a single material. However, it is more efficient to reuse three isomers of the diiodo compound, namely, para (p-), ortho (o-), and meta (m-) which are separated and purified through several steps of distillation, crystallization, and solid-liquid separation of the reaction products of non-halogenated aromatic compound, diiodo compound thereof, monoiodo compound thereof, and iodine.

Meanwhile, the non-halogenated aromatic compound used in the process according to the above embodiment is determined depending on the desired iodinated aromatic compound, and may be preferably selected from the group consisting of benzene, naphthalene, and biphenyl without limitation. Therefore, the reactant, monoiodo aromatic compound may be preferably selected from the group consisting of monoiodo benzene, monoiodo naphthalene, and monoiodo biphenyl. In addition, the diiodo aromatic compound may be also preferably selected from the group consisting of diiodo benzene, diiodo naphthalene and diiodo biphenyl.

In this connection, the molar ratio of aromatic/iodine (aromatic/I) represents the molar ratio of the aromatic compound and iodine which are used under the reaction conditions. Upon the preparation of the diiodo compound, the non-halogenated aromatic compound should be reacted with 1 mole of iodine molecule (two iodine atoms). In this regard, the molar ratio of aromatic/iodine is defined as in the following Equation 1.

$$\text{aromatic/iodine} = \frac{[(\text{the number of moles of non-halogenated aromatic compound} \times 2) + (\text{the number of moles of monoiodo compound})]}{(\text{the number of moles of iodine molecule} \times 2)} \quad [\text{Equation 1}]$$

In the process for preparing iodinated aromatic compounds according to the above embodiment of the present invention, the composition of feed materials is not particularly limited, as long as the ratio of aromatic/iodine satisfies 1 or more. If a large amount of iodine is used, the productivity of the multi-iodinated aromatic compound is increased while the conversion rate of iodine is lower. However, if a large amount of the non-halogenated aromatic compound with respect to iodine is used in order to increase the conversion rate of iodine, the conversion rate of iodine can be increased, while the productivity of the diiodo compound is decreased. Therefore, it is preferable that the molar ratio is appropriately controlled to perform the reaction, considering the object. Therefore, the aromatic compound and iodine are preferably supplied at a molar ratio of 0.8 to 3.0, and more preferably, 1.5 to 2.4.

Meanwhile, as the feeding concentration of diiodo compound is increased, the composition of by-products is constantly maintained, the reaction temperature is also stably controlled, and the conversion rate of iodine is also increased. Preferably, the diiodo compound may be introduced in an amount of 7 wt % to 45 wt %, and more preferably 11 wt % to 40 wt %, based on the total weight of the feed materials. If the diiodo compound is introduced at an amount of less than 7 wt %, it is hard to ensure the effects of adding the diiodo compound, including the reaction temperature control, suppression of side-reactions and high conversion rate of iodine. On the contrary, even though the diiodo compound is introduced at an amount of more than 45 wt %, the effects of adding the diiodo compound are not greatly improved, but constantly maintained, and the reactor temperature is problematically decreased, leading to a reduction in energy efficiency.

The iodinated aromatic compound to be prepared according to the above embodiment may be preferably, but is not limited to, diiodo benzene. More preferably, it may be commercially valuable para-diiodo benzene.

Meanwhile, the process of preparing iodinated aromatic compounds according to the above embodiment is carried out in the presence of a zeolite catalyst. The zeolite catalyst is hydrated aluminum silicates of alkali and alkaline earth metals, and its crystal structure and composition are not particularly limited. The zeolite catalyst may be preferably selected from the group consisting of Na-13X, Y-type, ZSM5 and K-13X, and more preferably Na-13X, which increases productivity of the diiodo compound.

According to the temperature profile in accordance with the process of preparing iodinated aromatic compounds according to the above embodiment of the present invention, as the reaction temperature increases, the conversion rates of the reactants (aromatic compound and iodine) increase, while the selectivity of the commercially valuable p-diiodo compound decreases. The reaction may be also carried out at a wide range of reaction pressure. As the reaction pressure increases, iodination efficiency increases. Considering the above features, the iodination may be conducted at the temperature of 230 to 350° C. and under the pressure from atmospheric pressure to 5 atm. The iodination may be preferably conducted at the temperature of 260 to 310° C., and more preferably 280 to 300° C. and under the pressure of atmosphere to 5 atm. When the reaction temperature is constantly maintained within the above range, productivity of the diiodo compound can be effectively improved while conversion rates of the reactants (aromatic compound and iodine) are maintained at a high level.

Meanwhile, the above described diiodo aromatic compound used as a reaction material may be a eutectic mixture of diiodo compounds obtained by separation and purification of reaction products that are produced according to the embodiments of the present invention. That is, the preparation process of iodinated aromatic compounds according to another embodiment of the present invention may further comprise the steps of recycling and iodination of the diiodo compound which is obtained by distillation, crystallization, and solid-liquid separation of the reaction products of the above iodination step. Since the process further comprises the above recycling step, the diiodo compound among the reaction products can be reused, thereby improving the process productivity.

In this regard, the method of reusing the diiodo compound may comprise the steps of:

separating and eliminating an aromatic compound from the reaction products of an aromatic compound, a monoiodo aromatic compound, a diiodo aromatic compound, and iodine, after the reaction products are transported to a first distillation column 10 from an iodination reactor 2;

transporting the residue distillate from the first distillation column 10 into a second distillation column 12, and separating the monoiodo compound and iodine from the distillate;

transporting the residue distillate from the second distillation column 12 into a third distillation column 14, separating a diiodo substituted mixture of para-diiodo compound, ortho-diiodo compound, and meta-diiodo compound from the distillate, and transporting the diiodo substituted mixture into a crystallization and solid-liquid separator 16;

separating a solid para-diiodo compound from the diiodo substituted mixture to recover a mother liquid including a liquid para-diiodo compound, ortho-diiodo compound, and meta-diiodo compound through the crystallization and solid-liquid separator 16; and recycling a portion of the mother liquid into the iodination reactor 2 to reuse the diiodo compound.

Figure 3:
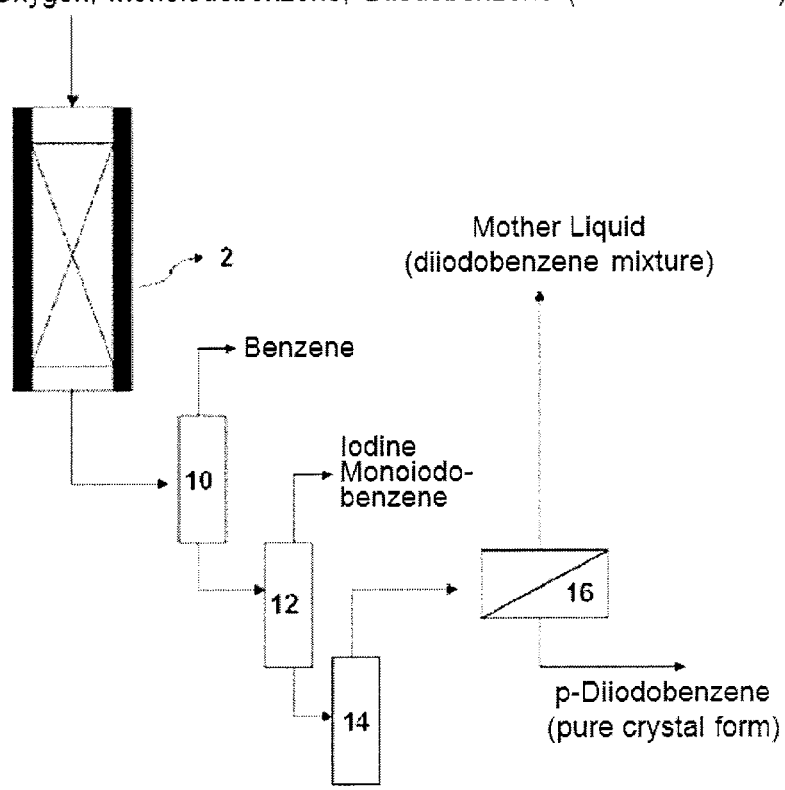
FIG. 3 is a schematic diagram showing the entire preparation process of iodinated aromatic compounds and the method of recycling a eutectic mixture of diiodo compounds according to other embodiment of the present invention.

As one Example of the above embodiments, the entire process using benzene, iodine, monoiodo benzene and diiodo benzene as reaction materials and the method of recycling a eutectic mixture of diiodo compounds are illustrated in FIG. 3. When the diiodo compound is recycled according to the embodiment, the amount of total diiodo compound obtained as the product is also increased, thereby greatly improving the economic efficiency and productivity.

In the above process for preparing iodinated aromatic compounds, iodination and iodine conversion simultaneously occur, and thus side-reactions are suppressed, the reaction temperature is also constantly maintained within the above range during the preparation process of iodinated aromatic compounds, thereby preventing formation of impurities such as carbon deposits due to combustion reaction of reaction materials, and shortening the replacement period of the catalyst, leading to the controlled formation of impurities through suppression of side-reactions. Particularly, in the preparation process of iodinated aromatic compounds according to the present invention, the conversion rate of $I_2$ may be preferably 80% or more, more preferably 83% or more, and furthermore preferably 85% or more. In the preparation process of iodinated aromatic compounds, the conversion rate of DIB, namely, total DIB production may be preferably 40 wt % or more, more preferably 41 wt % or more, and further more preferably 43 wt % or more.

Meanwhile, in the preparation process of iodinated aromatic compounds according to the present invention, iodination and iodine conversion simultaneously occur to prevent side-reactions, and lifetime of the iodination catalyst is extended by enabling stable reaction temperature control, leading to the controlled formation of impurities through suppression of side-reactions. Therefore, the preparation process can be widely used in the production of diiodo compound.

EXAMPLES

Hereinafter, the functions and the effects of the invention are explained in more detail, according to specific examples of the present invention. However, the following examples are only for explaining the present invention and the range of the present invention is not limited to or by them.

First, the concept of the terms used in the following Comparative Example 1 and Examples 1-3 to provide an evidence for the usefulness and effects of the present invention will be described. In particular, the concept of the terms for examining a reaction product and the efficiency of a reaction process will now be described.

Conversion Rate (%) of Iodine ($I_2$)

The conversion rate of iodine ($I_2$) is obtained by dividing the amount of iodine converted to the reaction product by the amount of iodine introduced, and then expressed as a percentage (%).

Conversion Rate (%) of Benzene

The conversion rate of benzene is also obtained by dividing the amount of benzene converted to the reaction product by the amount of benzene introduced, and then expressed as a percentage (%).

Productivity of Diiodo Benzene (Total DIB, Wt %)

Iodinated benzenes produced through the iodination reaction can be classified into the following compounds: monoiodobenzene (MIB) obtained by reaction with one iodine atom; diiodobenzene (DIB) obtained by reaction with two iodine atoms; and triiodobenzene (TIB) obtained by reaction with three iodine atoms. Among them, each of diiodobenzene (DIB) and triiodobenzene (TIB) may have three isomers. That is, for diiodobenzenes, three isomers of para (p-), ortho (o-) and meta (m-) diiodobenzenes are produced by the iodination reaction.

Herein, total diiodobenzene (Total DIB) refers to the sum of the weight percentages of p-, o- and m-diiodobenzenes contained in the reaction product, and is defined by the following Equation 2:

Total DIB (wt %)=[(p-DIB+m-DIB+o-DIB)/Total Products]×100    [Equation 2]

Comparative Example 1

In an iodinating reactor 2 as shown in FIG. 1, benzene (111.2 g/hr), iodine (73.15 g/hr), monoiodo benzene (527.4 g/hr), and oxygen were used as reaction materials to perform iodination in the presence of Na-13X zeolite catalyst without addition of diiodo benzene. At this time, the molar ratio of non-halogenated aromatic compound/iodine introduced was 1.93.

First, iodine and oxygen were preheated to approximately 200° C. through a preheater, and then introduced to the reactor. Further, benzene and monoiodo benzene were converted in the form of vapor through a vaporizer using other feeding line, and then preheated to approximately 200° C. and introduced to the reactor. The reaction temperature was controlled by controlling the temperature of oil supplied to the oil jacket of the reactor, and the center of the reactor was maintained at a temperature of 280° C. However, all areas of the reactor were not maintained at a constant temperature. The temperature of the upper part of the reactor increased to approximately 320° C., which was an undesirably excessive temperature rise. The reaction temperature decreased to approximately 240° C. along with the flow direction of the reactant.

Figure 4:
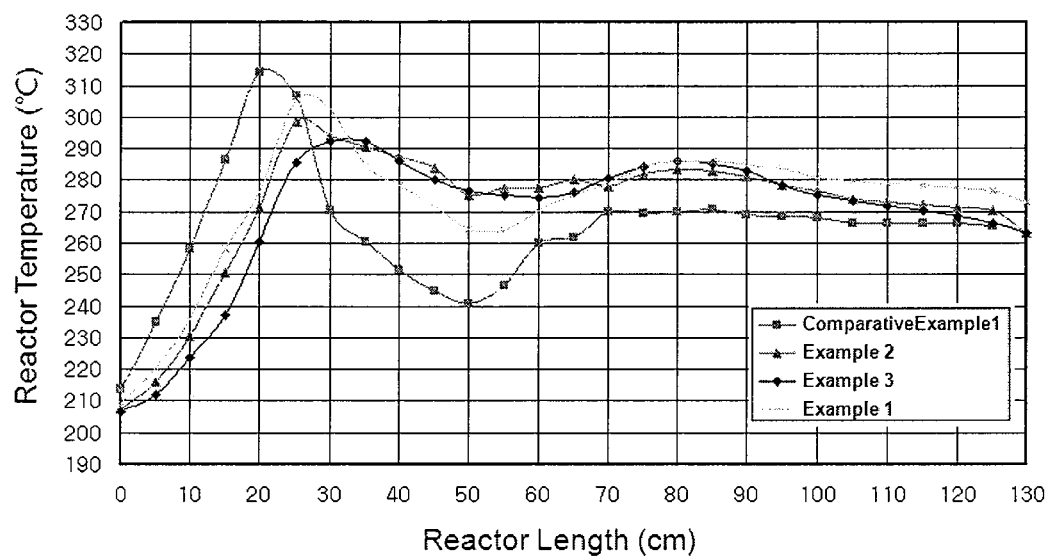
FIG. 4 is a graph showing temperature distribution according to a length of the reactor during the reaction process according to Examples 1 to 3 and Comparative Example 1 of the present invention.

Specifically, to examine temperature profile of the reactor, a temperature measuring instrument such as a thermowell or a thermocouple was installed at the center of the reactor, and the temperature of the upper, middle, and lower parts of the reactor was then periodically examined using the movable thermocouple, which can move upward and downward of the reactor to determine the highest temperature region. A temperature distribution graph according to a length of the reactor, measured at the center of the reactor, is shown in FIG. 4.

The iodination reaction was performed at atmospheric pressure by continuous process, and sampling and analyzing were performed 24 hrs after reaching the reaction conditions. The reaction conditions and results are shown in the following Table 1.

Example 1

In the equipment as shown in FIG. 2, benzene (102.4 g/hr), iodine (66.9 g/hr), and monoiodo benzene (483.8 g/hr) were introduced to perform iodination in the presence of Na-13X zeolite catalyst under the same conditions as in Comparative Example 1. In addition, diiodo benzene (65.9 g/hr) was also introduced, in which the composition of diiodo benzene was 9% (wt %), based on the total feed materials. At this time, the molar ratio of non-halogenated aromatic compound/iodine introduced was 1.93. The diiodo benzene used herein was not a single material, but a liquid diiodo benzene mixture (para, ortho, meta) obtained by crystallization and solid/liquid separation of three isomers of diiodo benzene (para, ortho, meta).

Further, a temperature distribution graph according to a length of the reactor, measured at the center of the reactor in the same manner as in Comparative Example 1, is shown in FIG. 4. The reaction conditions and data of the reaction products are shown in the following Table 1.

In particular, all areas of the reactor were maintained at an almost constant temperature. The temperature of the upper part of the reactor was maintained at approximately 310° C. or lower, which is close to the desired temperature. The reaction temperature was also maintained at approximately 260° C. or higher along with the flow direction of the reactant.

Example 2

In the equipment as shown in FIG. 2, benzene (98.1 g/hr), iodine (47.8 g/hr), and monoiodo benzene (458.7 g/hr) were introduced to perform iodination in the presence of Na-13X zeolite catalyst under the same conditions as in Comparative Example 1. In addition, diiodo benzene (115.1 g/hr) was also introduced, and the composition of diiodo benzene was 16% (wt %), based on the total feed materials. At this time, the molar ratio of non-halogenated aromatic compound/iodine introduced was 1.93.

Further, a temperature distribution graph according to a length of the reactor, measured at the center of the reactor in the same manner as in Comparative Example 1, is shown in FIG. 4. The reaction conditions and data of the reaction products are shown in the following Table 1.

In particular, all areas of the reactor were maintained at an almost constant temperature. The temperature of the upper part of the reactor was maintained at approximately 300° C. or lower, which is close to the desired temperature. The reaction temperature was also maintained at approximately 275° C. or higher along with the flow direction of the reactant.

Example 3

In the equipment as shown in FIG. 2, benzene (91.3 g/hr), iodine (47.87 g/hr), and monoiodo benzene (422.7 g/hr) were introduced to perform iodination in the presence of Na-13X zeolite catalyst under the same conditions as in Comparative Example 1. In addition, diiodo benzene (162.2 g/hr) was also introduced, and the composition of diiodo benzene was 22%

(wt %), based on the total feed materials. At this time, the molar ratio of non-halogenated aromatic compound/iodine introduced was 1.93.

Further, a temperature distribution graph according to a length of the reactor, measured at the center of the reactor in the same manner as in Comparative Example 1, is shown in FIG. 4. The reaction conditions and data of the reaction products are shown in the following Table 1.

In particular, all areas of the reactor were maintained at an almost constant temperature. The temperature of the upper part of the reactor was maintained at approximately 300° C. or lower, which is close to the desired temperature. The reaction temperature was also maintained at approximately 275° C. or higher along with the flow direction of the reactant.

TABLE 1

| | | Comparative Example 1 | Example 1 | Example 2 | Example 3 |
|---|---|---|---|---|---|
| Feed conditions | | | | | |
| Benzene | g/hr | 111.24 | 102.44 | 98.13 | 91.28 |
| Iodine | g/hr | 73.15 | 66.87 | 47.81 | 47.87 |
| Monoiodo benzene | g/hr | 527.43 | 483.78 | 458.78 | 422.72 |
| Aromatic/Iodine | molar ratio | 1.93 | 1.93 | 1.93 | 1.93 |
| Diiodo benzene | g/hr | 0 | 65.9 | 115.1 | 162.2 |
| Product composition | | | | | |
| Benzene | wt % | 3.73 | 4.09 | 3.56 | 3.95 |
| Monoiodo benzene | wt % | 43.61 | 41.46 | 39.35 | 38.5 |
| p-DIB | wt % | 29.08 | 27.47 | 27.35 | 27.31 |
| m-DIB | wt % | 7.18 | 10.96 | 13.66 | 13.71 |
| o-DIB | wt % | 1.34 | 2.58 | 2.64 | 2.69 |
| TIB | wt % | 4.17 | 5.39 | 7.52 | 7.61 |
| other | wt % | 10.89 | 8.05 | 5.92 | 6.23 |
| Characteristics | | | | | |
| Conversion rate of $I_2$ | % | 75.39 | 83.3 | 87.8 | 87.22 |
| Conversion rate of benzene | % | 66.4 | 59.56 | 64.1 | 63.71 |
| Total DIB | wt % | 37.60 | 41.01 | 43.65 | 43.75 |

As shown in Table 1, even though the feeding amount of diiodo benzene was increased, there are little differences between Comparative Example 1 and Examples 1 to 3 regarding the compositions of the reaction products, para-, ortho-, and meta-diiodo benzene and triiodo benzene, and the compositions converged on a specific composition, indicating that iodination and iodine conversion of diiodo benzene and triiodo benzene into monoiodo benzene simultaneously occur in the presence of iodination catalyst. That is, it can be seen that side-reactions are suppressed by simultaneous process of iodination and iodine conversion.

Even though the difference in the production of para-diiodo benzene between Examples 1 to 3 and Comparative Example 1 (no addition of diiodo benzene) was about 2 wt %, there was a considerable difficulty in the reaction temperature control upon performing the preparation by Comparative Example 1. As shown in FIG. 4, Comparative Example 1 showed a great difference in temperature distribution according to a length of the reactor, which was measured at the center of the reactor, indicating that active reaction was localized in the specific region of the reactor and thus the entire catalyst layer was not efficiently used. On the contrary, Examples 1 to 3 showed little difference in temperature distribution according to a length of the reactor, indicating that the entire catalyst layer filled in the reactor was efficiently used.

In Comparative Example 1, the active reaction was localized in the specific region of the reactor and thus a portion of the catalyst was only used to accelerate catalyst inactivation in the region, which shortens the length of reactive catalyst layer in the entire catalyst layer. In addition, if temperature of the specific region of the reactor increases, a part of the reaction components is carbonized to rapidly reduce the activity of the catalyst, thus shortening the lifetime of the catalyst.

Meanwhile, from Example 1 to Example 3, the reaction temperature was more stably controlled, and by-products resulting from side-reactions were maintained at a constant level. It can be seen that the conversion rate of $I_2$ was increased, as the feeding amount of diiodo benzene became higher, compared to that of Comparative Example 1, which contributes to stable operation of distillation column in the refining process after the reaction.

As demonstrated in the above experimental results, when iodination is performed to prepare iodinated aromatic compounds by addition of diiodo compound to the reactants according to Examples 1 to 3 of the present invention, iodination and iodine conversion simultaneously occur to prevent side-reactions, and lifetime of the iodination catalyst is extended by enabling stable reaction temperature control. Therefore, the process is suitable for mass production of diiodo compound and also the commercially valuable para-diiodo compound, and thus it can be widely used for the production of diiodo compound, in particular, para-diiodo compound.

What is claimed is:

1. A process for preparing iodinated aromatic compounds, comprising:
   performing an iodination of a non-halogenated aromatic compound using a mixture of a monoiodo aromatic compound, a diiodo aromatic compound, and iodine in the presence of a zeolite catalyst under oxygen atmosphere;
   wherein the diiodo aromatic compound and a triiodo aromatic compound are converted into the monoiodo aromatic compound approximately simultaneously with the iodination, and
   wherein a molar ratio of the non-halogenated aromatic compound to the iodine, as introduced, is about 0.8 to about 3.0.

2. The process for preparing iodinated aromatic compounds according to claim 1, wherein the non-halogenated aromatic compound is selected from the group consisting of benzene, naphthalene, and biphenyl.

3. The process for preparing iodinated aromatic compounds according to claim 1, wherein the monoiodo aromatic compound is selected from the group consisting of monoiodo benzene, monoiodo naphthalene, and monoiodo biphenyl.

4. The process for preparing iodinated aromatic compounds according to claim 1, wherein the diiodo aromatic compound is selected from the group consisting of diiodo benzene, diiodo naphthalene, and diiodo biphenyl.

5. The process for preparing iodinated aromatic compounds according to claim 1, wherein the diiodo aromatic compound is introduced in the range of about 7 wt % to about 45 wt %, based on the total weight of the feed materials.

6. The process for preparing iodinated aromatic compounds according to claim 1, wherein the iodinated aromatic compounds produced by the iodination step comprise diiodo benzene.

7. The process for preparing iodinated aromatic compounds according to claim 6, wherein the diiodo benzene is para-diiodo benzene.

8. The process for preparing iodinated aromatic compounds according to claim 1, wherein the zeolite catalyst is selected from the group consisting of Na-13X, Y-type, ZSM5, and K-13X.

9. The process for preparing iodinated aromatic compounds according to claim 8, wherein the zeolite catalyst is Na-13X.

10. The process for preparing iodinated aromatic compounds according to claim 1, wherein the iodination is performed at the temperature of about 230° C. to about 350° C. and under the pressure of atmosphere to 5 atm.

11. The process for preparing iodinated aromatic compounds according to claim 1, wherein the iodination is performed at the temperature of about 275° C. to about 290° C. and under the pressure of atmosphere to 5 atm.

12. The process for preparing iodinated aromatic compounds according to claim 1, further comprising the step of recycling a diiodo compound to perform the iodination, wherein the diiodo compound are obtained from a distillation, a crystallization, and a solid-liquid separation by using the reaction products of the iodination step.

13. The process for preparing iodinated aromatic compounds according to claim 12, wherein the process comprises the steps of:
    separating the non-halogenated aromatic compound from reaction products of the non-halogenated aromatic compound, the monoiodo aromatic compound, the diiodo aromatic compound, and the iodine, after the reaction products are transported to a first distillation column 10 from an iodination reactor 2 ;
    transporting the residue distillate from the first distillation column 10 into a second distillation column 12, and separating the monoiodo compound and iodine from the distillate;
    transporting the residue distillate from the second distillation column 12 into a third distillation column 14, separating a diiodo substituted mixture of para-diiodo compound, ortho-diiodo compound, and meta-diiodo compound from the distillate, and transporting the diiodo substituted mixture into a crystallization and solid-liquid separator 16;
    separating a solid para-diiodo compound from the diiodo substituted mixture to recover a mother liquid including a liquid para-diiodo compound, ortho-diiodo compound, and meta- diiodo compound through the crystallization and solid-liquid separator 16; and
recycling a portion of the mother liquid into the iodination reactor 2 to reuse the diiodo compound.

14. The process for preparing iodinated aromatic compounds according to claim 1, wherein a molar ratio of non-halogenated aromatic compound to iodine, as introduced, is about 1.5 to about 2.4.

15. The process for preparing iodinated aromatic compounds according to claim 1, wherein the diiodo aromatic compound is introduced at about 11 wt % to about 40 wt % based on the total weight of the feed materials.

16. The process for preparing iodinated aromatic compounds according to claim 1, wherein the conversion rate of $I_2$ is 80% or more.

* * * * *

UNITED STATES PATENT AND TRADEMARK OFFICE
CERTIFICATE OF CORRECTION

PATENT NO. : 8,614,362 B2  
APPLICATION NO. : 13/133904  
DATED : December 24, 2013  
INVENTOR(S) : Lee et al.

It is certified that error appears in the above-identified patent and that said Letters Patent is hereby corrected as shown below:

In the Claims

In column 11, line 30, in claim 13, delete "2 ;" and insert --2;--, therefor

In column 12, line 15, in claim 13, delete "meta- diiodo" and insert --meta-diiodo--, therefor Signed and Sealed this  
Twentieth Day of May, 2014

Michelle K. Lee  
*Deputy Director of the United States Patent and Trademark Office*